(12) United States Patent
Stähler et al.

(10) Patent No.: US 9,568,839 B2
(45) Date of Patent: *Feb. 14, 2017

(54) METHOD FOR PRODUCING POLYMERS

(75) Inventors: Peer F. Stähler, Mannheim (DE); Cord F. Stähler, Hirshberg a.d. Bergstrasse/Grossachsen (DE); Manfred Müller, Ladenburg (DE)

(73) Assignee: Synthetic Genomics, Inc., La Jolla, CA (US)

( * ) Notice: Subject to any disclaimer, the term of this patent is extended or adjusted under 35 U.S.C. 154(b) by 67 days.

This patent is subject to a terminal disclaimer.

(21) Appl. No.: 12/400,493

(22) Filed: Mar. 9, 2009

(65) Prior Publication Data

US 2009/0170802 A1   Jul. 2, 2009

Related U.S. Application Data

(60) Continuation of application No. 11/785,505, filed on Apr. 18, 2007, now abandoned, which is a division of
(Continued)

(30) Foreign Application Priority Data

Feb. 19, 1999  (DE) .................................. 199 07 080
Jun. 24, 1999  (DE) .................................. 199 28 843
(Continued)

(51) Int. Cl.
*B01J 19/00* (2006.01)
*G03F 7/20* (2006.01)
(Continued)

(52) U.S. Cl.
CPC ........ *G03F 7/70216* (2013.01); *B01J 19/0046* (2013.01); *B01J 19/0093* (2013.01);
(Continued)

(58) Field of Classification Search
CPC ................ B01J 19/0046; B01J 19/0093; B01J 2219/00317; B01J 2219/00432; B01J 2219/00436; B01J 2219/00439; B01J 2219/00441; B01J 2219/00448; B01J 2219/00479; B01J 2219/00497; B01J 2219/00511; B01J 2219/00529
See application file for complete search history.

(56) References Cited

U.S. PATENT DOCUMENTS 4,689,405 A   8/1987 Frank et al.
5,143,854 A   9/1992 Pirrung et al.
(Continued)

FOREIGN PATENT DOCUMENTS

EP   0022242   1/1981
EP   0130166   1/1985
(Continued)

OTHER PUBLICATIONS

Hayden, M. A. et al., DNA, vol. 7, pp. 571-577 (1988).*
(Continued)

*Primary Examiner* — Teresa Strzelecka
(74) *Attorney, Agent, or Firm* — DLA Piper LLP (US)

(57) ABSTRACT

The invention relates to a method for producing polymers, in particular synthetic nucleic acid double strands of optional sequence, comprising the steps:
(a) provision of a support having a surface area which contains a plurality of individual reaction areas,
(b) location-resolved synthesis of nucleic acid fragments having in each case different base sequences in several of the individual reaction areas, and
(c) detachment of the nucleic acid fragments from individual reaction areas.

6 Claims, 7 Drawing Sheets

Related U.S. Application Data application No. 10/455,369, filed on Jun. 6, 2003, now Pat. No. 7,790,369, which is a division of application No. 09/869,332, filed as application No. PCT/EP00/01356 on Feb. 18, 2000, now Pat. No. 6,586,211.

(30) Foreign Application Priority Data

| Aug. 27, 1999 | (DE) | 199 40 752 |
|---|---|---|
| Aug. 27, 1999 | (WO) | PCT/EP99/06316 |
| Nov. 26, 1999 | (DE) | 199 57 116 |

(51) Int. Cl.

| B01L 3/00 | (2006.01) |
|---|---|
| B82Y 30/00 | (2011.01) |
| C12N 15/10 | (2006.01) |
| C12N 15/66 | (2006.01) |
| C12P 19/34 | (2006.01) |
| C12Q 1/68 | (2006.01) |
| C40B 40/06 | (2006.01) |
| C40B 40/10 | (2006.01) |
| C40B 50/14 | (2006.01) |

(52) U.S. Cl.

CPC ....... B01L 3/5085 (2013.01); B01L 3/502707 (2013.01); B82Y 30/00 (2013.01); C12N 15/10 (2013.01); C12N 15/66 (2013.01); C12P 19/34 (2013.01); *B01J 2219/0059* (2013.01); *B01J 2219/00317* (2013.01); *B01J 2219/00432* (2013.01); *B01J 2219/00436* (2013.01); *B01J 2219/00439* (2013.01); *B01J 2219/00441* (2013.01); *B01J 2219/00448* (2013.01); *B01J 2219/00479* (2013.01); *B01J 2219/00497* (2013.01); *B01J 2219/00511* (2013.01); *B01J 2219/00529* (2013.01); *B01J 2219/00585* (2013.01); *B01J 2219/00596* (2013.01); *B01J 2219/00603* (2013.01); *B01J 2219/00605* (2013.01); *B01J 2219/00608* (2013.01); *B01J 2219/00621* (2013.01); *B01J 2219/00626* (2013.01); *B01J 2219/00648* (2013.01); *B01J 2219/00659* (2013.01); *B01J 2219/00675* (2013.01); *B01J 2219/00689* (2013.01); *B01J 2219/00702* (2013.01); *B01J 2219/00704* (2013.01); *B01J 2219/00711* (2013.01); *B01J 2219/00722* (2013.01); *B01J 2219/00725* (2013.01); *B01L 2300/069* (2013.01); *B01L 2300/0654* (2013.01); *B01L 2300/0864* (2013.01); *C40B 40/06* (2013.01); *C40B 40/10* (2013.01); *C40B 50/14* (2013.01)

(56) References Cited

U.S. PATENT DOCUMENTS

| 5,474,796 | A | 12/1995 | Brennan |
|---|---|---|---|
| 5,510,270 | A | 4/1996 | Fodor et al. |
| 5,624,711 | A | 4/1997 | Sundberg et al. |
| 5,674,742 | A | 10/1997 | Northrup et al. |
| 5,677,195 | A | 10/1997 | Winkler et al. |
| 5,723,320 | A | 3/1998 | Dehlinger |
| 5,755,942 | A | 5/1998 | Zanzucchi et al. |
| 5,922,591 | A | 7/1999 | Anderson et al. |
| 6,013,440 | A | 1/2000 | Lipshutz et al. |
| 6,020,481 | A | 2/2000 | Benson et al. |
| 6,238,884 | B1 | 5/2001 | Short et al. |
| 6,348,353 | B1 | 2/2002 | Harrington et al. |
| 6,586,211 | B1 | 7/2003 | Stahler et al. |
| 7,097,974 | B1 | 8/2006 | Stähler et al. |

FOREIGN PATENT DOCUMENTS

| EP | 0316018 | 5/1989 |
|---|---|---|
| EP | 0385410 | 9/1990 |
| EP | 1 117 478 B1 | 7/2001 |
| EP | 1 405 666 B1 | 4/2004 |
| EP | 1015576 B1 | 4/2005 |
| EP | 1159285 B1 | 5/2005 |
| EP | 1153127 B1 | 7/2006 |
| WO | WO 9000626 | 1/1990 |
| WO | WO 94/12632 | 6/1994 |
| WO | 9418226 A1 | 8/1994 |
| WO | WO 95/17413 | 6/1995 |
| WO | WO 97/42330 | 11/1997 |
| WO | WO 99/14318 | 3/1999 |
| WO | 9925724 A2 | 5/1999 |
| WO | WO 00/13017 | 3/2000 |

OTHER PUBLICATIONS

Ferretti, L. et al., PNAS USA, vol. 83, pp. 599-603 (1986).*
AB Model 380A DNA Sythesizer, Nucl. Acids Res., vol. 12, pp. 1-16 (1984).*
Weiler, J. et al, "Combining the Preparation of Oligonucleotide Arrays and Synthesis of High-Quality Primers," Analytical Biochemistry 243, 218-227 (1996) Article No. 0509, Copyright 1996 by Academic Press, Inc.
Mullis, K. et al., "Specific Enzymatic Amplification of DNA In Vitro: The Polymerase Chain Reaction," Cold Spring Harbor Symposia on Quantitative Biology, vol. L1, pp. 263-273, Copyright 1986 Cold Spring Harbor Laboratory.
Khudyakov, Y.E. et al., "Synthetic Gene for the Hepatitis C Virus Nucleocapsid Protein," Nucl. Acids Res., vol. 21, pp. 2747-2754 (1993).
Beattie, K.L. and Fowler, R.F., "Solid-phase gene assembly", Nature, vol. 352, pp. 548, 549 (1991).
Rayner, S. et al., "MerMade: An oligodeoxyribonucleotide synthesizer for high throughput oligonucleotide production in dual 96-well plates" PCR Methods and Applications, US, Cold Spring Harbor, NY, vol. 8, No. 7, Jul. 1, 1998, pp. 741-747.
Sindelar, L.E. and Jaklevic, J.M., "High-throughput DNA synthesis in a multichannel format" Nucleic Acids Research, GB, Oxford University Press, Surrey, vol. 23, No. 6, Jan. 1, 1995, pp. 982-987.
Lashkari D.A., et al., "An Automated Multiplex Oligonucleotide Synthesizer: Development of High-Throughput, Low-Cost DNA Synthesis" Proceedings of the National Academy of Sciences of USA, US, National Academy of Science, Washington, vol. 92, No. 17, Aug. 15, 1995, pp. 7912-7915.
Stemmer, W.P.C., et al., "Single-step assembly of a gene and entire plasmid from large numbers of oligodeoxyribonucleotides", Gene, vol. 164, pp. 49-53 (1995).
Beattie, K.L. et al., "Solid-phase gene assembly," Nature, vol. 352, pp. 548-549 (1991).
English translation of EP 1 153 127 as filed at UK Patent Office (E10).

* cited by examiner

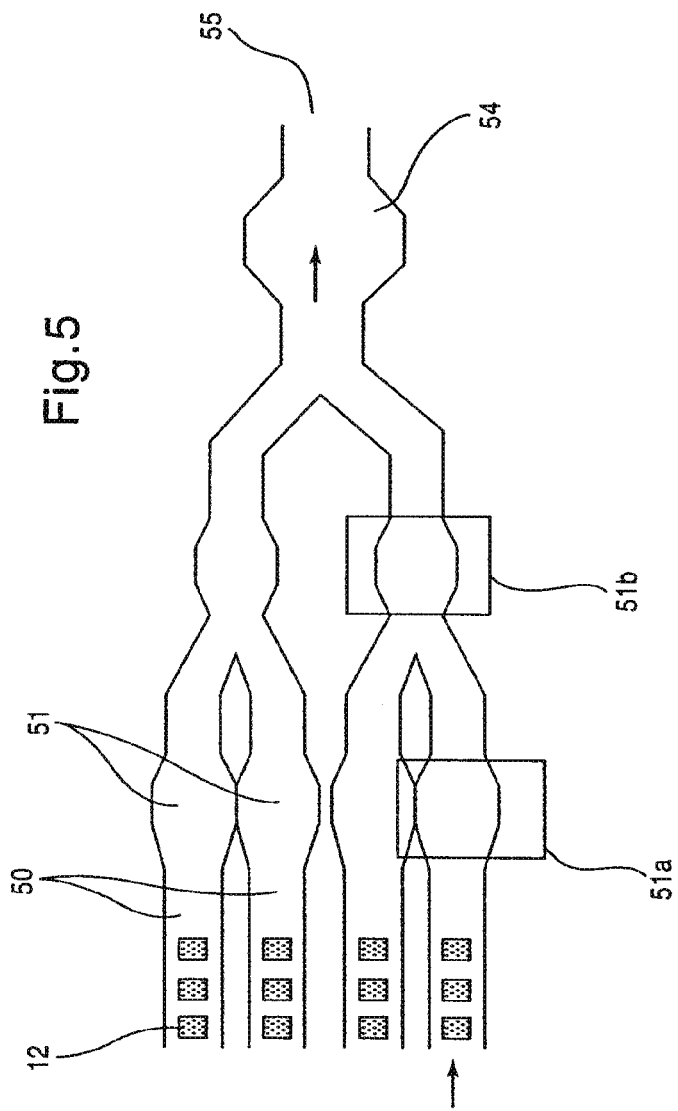

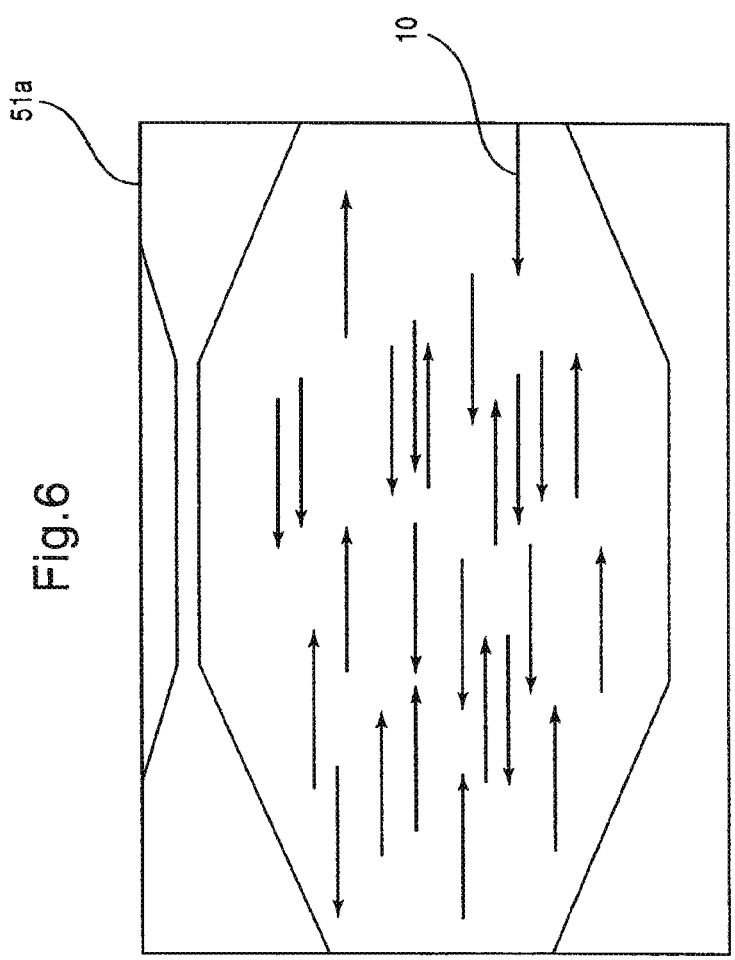

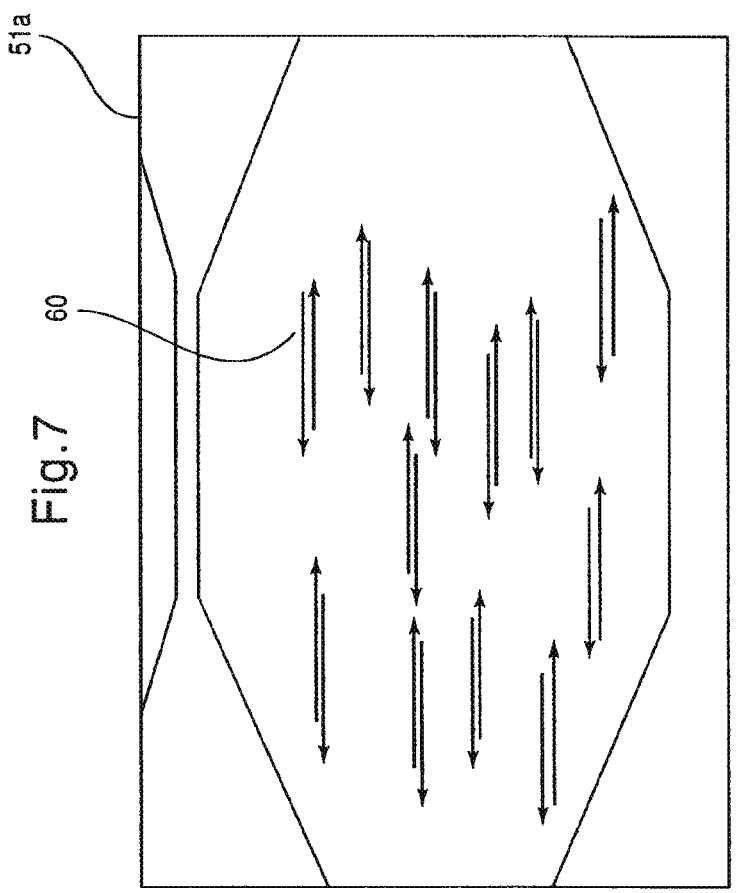

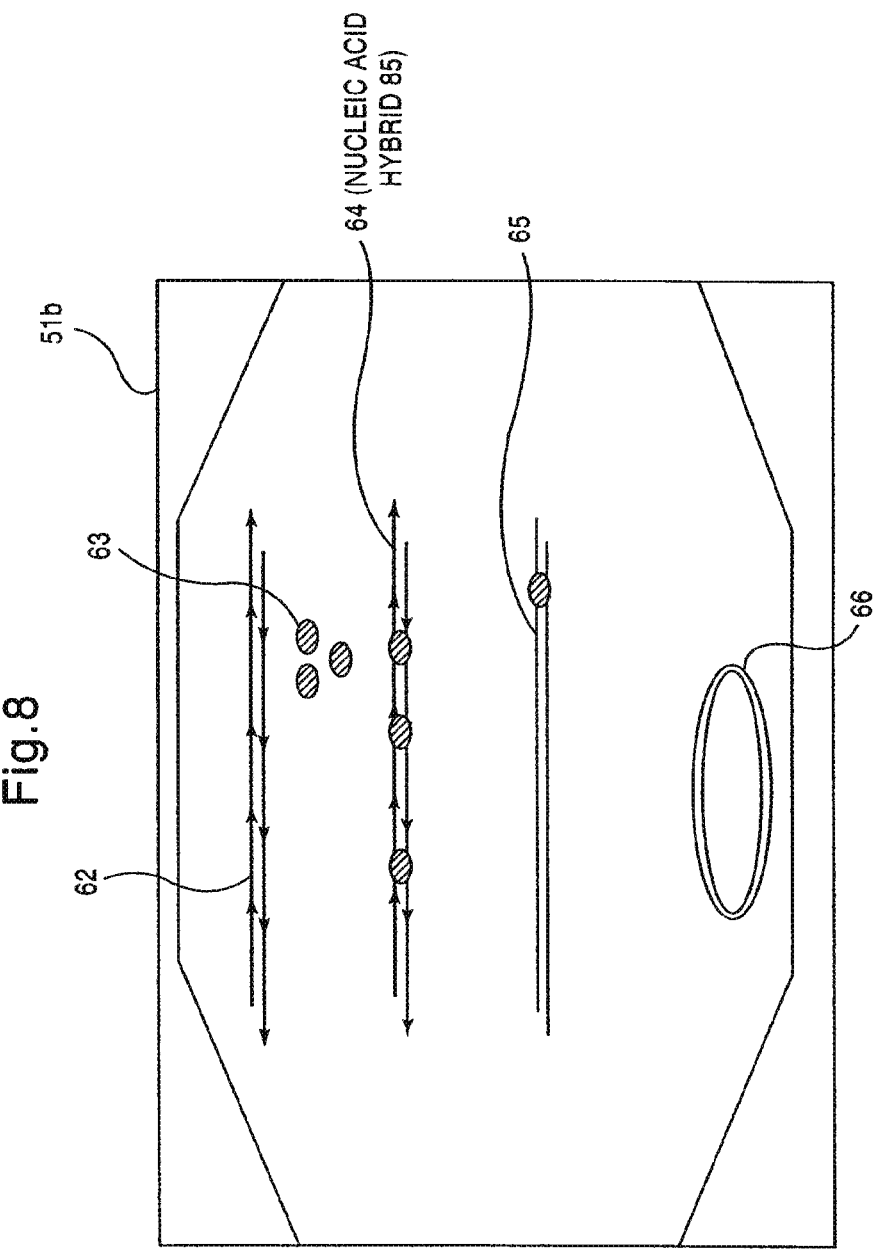

METHOD FOR PRODUCING POLYMERS

CROSS-REFERENCE TO RELATED APPLICATIONS

The present application is a continuation of application Ser. No. 11/785,505 filed on 18 Apr. 2007, which in turn is a divisional of application Ser. No. 10/455,369 filed on 6 Jun. 2003, which in turn is a divisional of application Ser. No. 09/869,332 filed on 26 Jul. 2001, now U.S. Pat. No. 6,586,211, which in turn is a national stage filing under 35 U.S.C. §371 of PCT/EP00/01356 filed on 18 Feb. 2000, which claims priority to German patent application No. 199 57 116.3 filed on 26 Nov. 1999, International patent application No. PCT/EP99/06316 filed on 27 Aug. 1999, German patent application No. 199 40 752.5 filed on 27 Aug. 1999, German patent application No. 199 28 843.7 filed on 24 Jun. 1999 and German patent application No. 199 07 080.6 filed on 19 Feb. 1999.

The invention relates to a method for producing polymers, in particular synthetic nucleic acid double strands of optional sequence.

TECHNICAL BACKGROUND OF THE INVENTION

Manipulation and construction of genetic elements such as, for example, gene fragments, whole genes or regulatory regions through the development of DNA recombination technology, which is often also referred to as genetic engineering, led to a particular need for genetic engineering methods and further development thereof in the areas of gene therapy, molecular medicine (basic research, vector development, vaccines, regeneration, etc.). Important areas of application are also the development of active substances, production of active substances in the context of the development of pharmaceuticals, combinatorial biosynthesis (antibodies, effectors such as growth factors, neural transmitters, etc.), biotechnology (e.g. enzyme design, pharming, biological production methods, bioreactors, etc.), diagnostics (BioChips, receptors/antibodies, enzyme design, etc.) and environmental technology (specialized or custom microorganisms, production processes, cleaning-up, sensors, etc.).

PRIOR ART

Numerous methods, first and foremost enzyme-based methods, allow specific manipulation of DNA for different purposes.

All of said methods have to use available genetic material. Said material is, on the one hand, well-defined to a large extent but allows, on the other hand, in a kind of "construction kit system" only a limited amount of possible combinations of the particular available and slightly modified elements.

In this connection, completely synthetic DNA has so far played only a minor part in the form of one of these combinatorial elements, with the aid of which specific modifications of the available genetic material are possible.

The known methods share the large amount of work required, combined with a certain duration of appropriate operations, since the stages of molecular biological and in particular genetic experiments such as DNA isolation, manipulation, transfer into suitable target cells, propagation, renewed isolation, etc. usually have to be repeated several times. Many of the operations which come up can only insufficiently be automated and accelerated so that the corresponding work remains time-consuming and labor-intensive. For the isolation of genes, which must precede functional study and characterization of the gene product, the flow of information is in most cases from isolated RNA (mRNA) via cDNA and appropriate gene libraries via complicated screening methods to a single clone. The desired DNA which has been cloned in said clone is frequently incomplete, so that further screening processes follow.

Finally, the above-described recombination of DNA fragments has only limited flexibility and allows, together with the described amount of work required, only few opportunities for optimization. In view of the variety and complexity in genetics, functional genomics and proteomics, i.e. the study of gene product actions, such optimizations in particular are a bottleneck for the further development of modern biology.

A common method is recombination by enzymatic methods (in vitro): here, DNA elements (isolated genomic DNA, plasmids, amplicons, viral or bacterial genomes, vectors) are first cut into fragments with defined ends by appropriate restriction enzymes. Depending on the composition of these ends, it is possible to recombine the fragments formed and to link them to form larger DNA elements (likewise enzymatically). For DNA propagation purposes, this is frequently carried out in a plasmid acting as cloning vector.

The recombinant DNA normally has to be propagated clonally in suitable organisms (cloning) and, after this time-consuming step and isolation by appropriate methods, is again available for manipulations such as, for example, recombinations. However, the restriction enzyme cleavage sites are a limiting factor in this method: each enzyme recognizes a specific sequence on the (double-stranded) DNA, which is between three and twelve nucleotide bases in length, depending on the particular enzyme, and therefore, according to statistical distribution, a particular number of cleavage sites at which the DNA strand is cut is present on each DNA element. Cutting the treated DNA into defined fragments, which can subsequently be combined to give the desired sequence, is important for recombination. Sufficiently different and specific enzymes are available for recombination technology up to a limit of 10-30 kilo base pairs (kbp) of the DNA to be cut. In addition, preliminary work and commercial suppliers provide corresponding vectors which take up the recombinant DNA and allow cloning (and thus propagation and selection). Such vectors contain suitable cleavage sites for efficient recombination and integration.

With increasing length of the manipulated DNA, however, the rules of statistics give rise to the problem of multiple and unwanted cleavage sites. The statistical average for an enzyme recognition sequence of 6 nucleotide bases is one cleavage site per 4000 base pairs ($4^6$) and for 8 nucleotide bases it is one cleavage site per 65,000 ($4^8$). Recombination using restriction enzymes therefore is not particularly suitable for manipulating relatively large DNA elements (e.g. viral genomes, chromosomes, etc.).

Recombination by homologous recombination in cells is known, too. Here, if identical sequence sections are present on the elements to be recombined, it is possible to newly assemble and manipulate relatively large DNA elements by way of the natural process of homologous recombination. These recombination events are substantially more indirect than in the case of the restriction enzyme method and, moreover, more difficult to control. They often give distinctly poorer yields than the above-described recombination using restriction enzymes.

A second substantial disadvantage is restriction to the identical sequence sections mentioned which, on the one hand, have to be present in the first place and, on the other hand, are very specific for the particular system. The specific introduction of appropriate sequences itself then causes considerable difficulties.

An additional well-known method is the polymerase chain reaction (PCR) which allows enzymatic DNA synthesis (including high multiplication) due to the bordering regions of the section to be multiplied indicating a DNA replication start by means of short, completely synthetic DNA oligomers ("primers"). For this purpose, however, these flanking regions must be known and be specific for the region lying in between. When replicating the strand, however, polymerases also incorporate wrong nucleotides, with a frequency depending on the particular enzyme, so that there is always the danger of a certain distortion of the starting sequence. For some applications, this gradual distortion can be very disturbing. During chemical synthesis, sequences such as, for example, the above-described restriction cleavage sites can be incorporated into the primers. This allows (limited) manipulation of the complete sequence. The multiplied region can now be in the region of approx. 30 kbp, but most of this DNA molecule is the copy of a DNA already present.

The primers are prepared using automated solid phase synthesis and are widely available, but the configuration of all automatic synthesizers known to date leads to the production of amounts of primer DNA (μmol-range reaction mixtures) which are too large and not required for PCR, while the variety in variants remains limited.

Synthetic DNA Elements

Since the pioneering work of Khorana (inter alia in: Shabarova: Advanced Organic Chemistry of Nucleic Acids, VCH Weinheim;) in the 1960s, approaches in order to assemble double-stranded DNA with genetic or coding sequences from chemically synthesized DNA molecules have repeatedly been described. State of the art here is genetic elements of up to approx. 2 kbp in length which are synthesized from nucleic acids. Chemical solid phase synthesis of nucleic acids and peptides has been automated. Appropriate methods and devices have been described, for example, in U.S. Pat. No. 4,353,989 and U.S. Pat. No. 5,112,575.

Double-stranded DNA is synthesized from short oligonucleotides according to two methods (see Holowachuk et al., PCR Methods and Applications, Cold Spring Harbor Laboratory Press): on the one hand, the complete double strand is synthesized by synthesizing single-stranded nucleic acids (with suitable sequence), attaching complementary regions by hybridization and linking the molecular backbone by, for example, ligase. On the other hand, there is also the possibility of synthesizing regions overlapping at the edges as single-stranded nucleic acids, attachment by hybridization, filling in the single-stranded regions via enzymes (polymerases) and linking the backbone.

In both methods, the total length of the genetic element is restricted to only a few thousand nucleotide bases due to, on the one hand, the expenditure and production costs of nucleic acids in macroscopic column synthesis and, on the other hand, the logistics of nucleic acids being prepared separately in macroscopic column synthesis and then combined. Thus, the same size range as in DNA recombination technology is covered.

To summarize, the prior art can be described as a procedure in which, in analogy to logical operations, the available matter (in this case genetic material in the form of nucleic acids) studied and combined (recombination). The result of recombination experiments of this kind is then studied and allows conclusions, inter alia about the elements employed and their combined effect. The procedure may therefore be described as (selectively) analytical and combinatorial.

The prior art thus does not allow any systematic studies of any combinations whatsoever. The modification of the combined elements is almost impossible. Systematic testing of modifications is impossible.

SUBJECT OF THE INVENTION AND OBJECT ACHIEVED THEREWITH

It is intended to provide a method for directly converting digital genetic information (target sequence, databases, etc.) into biochemical genetic information (nucleic acids) without making use of nucleic acid fragments already present.

The invention therefore relates to a method for producing polymers, in which a plurality of oligomeric building blocks is synthesized on a support by parallel synthesis steps, is detached from the support and is brought into contact with one another to synthesize the polymer. Preference is given to synthesizing double-stranded nucleic acid polymers of at least 300 bp, in particular at least 1000 bp in length. The nucleic acid polymers are preferably selected from genes, gene clusters, chromosomes, viral and bacterial genomes or sections thereof. The oligomeric building blocks used for synthesizing the polymer are preferably 5-150, particularly preferably 5-30, monomer units in length. In successive steps, it is possible to detach in each case partially complementary oligonucleotide building blocks from the support and to bring them into contact with one another or with the polymer intermediate under hybridization conditions. Further examples of suitable polymers are nucleic acid analogs and proteins.

BRIEF DESCRIPTION OF THE DRAWINGS

FIG. 5 shows a top view of the arrangement of microchannels with fluidic reaction spaces 50, which contain the individual reaction areas, and reaction chambers, where a part sequence is assembled. In the reaction space 54 all microchannels within a reaction support are brought together. The final synthesis product is assembled there, too, and is removed through exit 55. The reference numbers 51a and 51b indicate the representations of a reaction chamber which are shown in enlarged form in FIG. 6 and FIG. 7 and FIG. 8. The arrows again signal the direction of flow.

FIG. 6 shows an enlarged representation of a reaction chamber 51a after a microchannel with detached single-stranded nucleic acids.

FIG. 7 shows an enlarged representation of a reaction chamber 51a after a microchannel with a double-stranded hybrid 60 composed of two attached complementary nucleic acid single strands.

FIG. 8 shows an enlarged representation of a reaction chamber 51b after bringing together two microchannels with an assembled double-stranded nucleic acid hybrid 62, enzyme 63 (e.g. ligases) for the covalent linkage of the building blocks of the nucleic acid hybrid 85, a linear covalently linked nucleic acid double strand 65 and a circular closed nucleic acid double strand 66 (e.g. vector).

Figure 1:
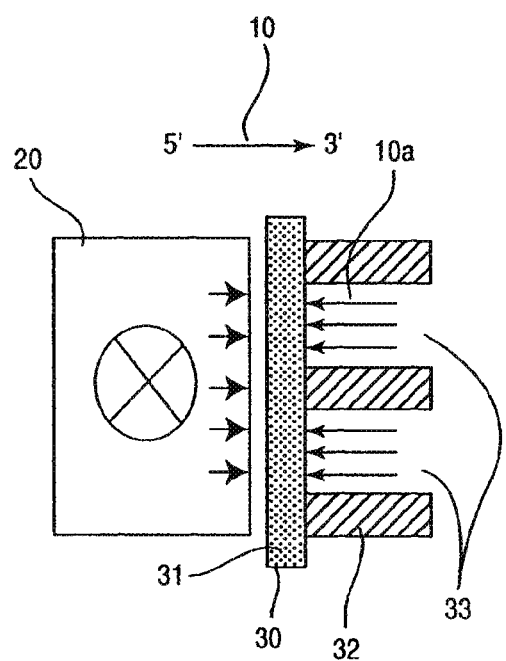
FIG. 1 shows a vertical section of a reaction support 30 which is orthogonal to the microchannels 33 present thereon, which are separated from one another by walls 32. The bottom 31 of the reaction support is transparent. Furthermore, a single-stranded nucleic acid 10 with the designation of the 5' and 3' ends according to convention is depicted diagrammatically. These are depicted as 10a with the 3' end covalently bound to the reaction support 30 by solid-phase synthesis. A light source matrix 20 with a light source and a controllable illumination exit facing the reaction support 30 is likewise depicted.
Figure 2:
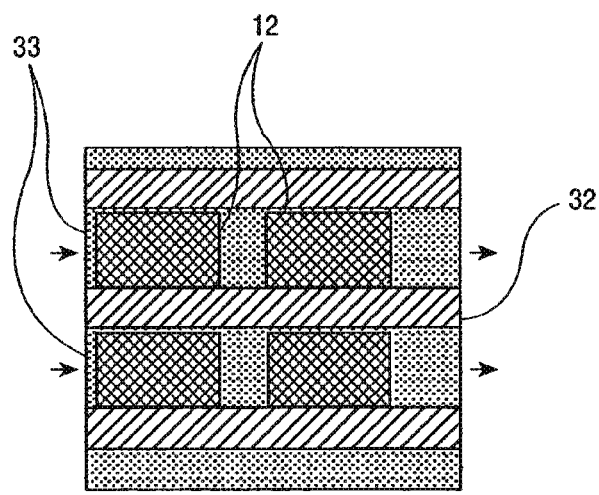
FIG. 2 shows a top view of reaction support 30 with reaction areas 12 and the walls 32 between the microchannels 33. The arrows indicate the direction of flow.
Figure 3:
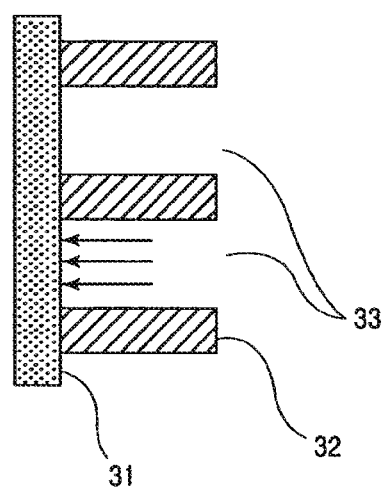
FIG. 3 shows, similar to FIG. 1, a vertical section through the reaction support 30, with the single-stranded nucleic acids in the microchannel 33 being detached.
Figure 4:
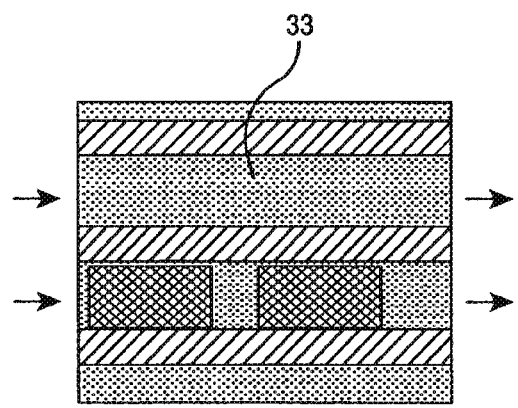
FIG. 4 again depicts a top view of the reaction support 30, with the single-stranded nucleic acids in the microchannel 33 being detached.

The reference number 64 represents a reaction of the enzymes with the nucleic acid hybrid.

DESCRIPTION OF THE INVENTION

In a particularly preferred embodiment, the invention relates to a method for producing synthetic DNA of any optional sequence and thus any known or novel functional genetic elements which are contained in said sequence. This method comprises the steps
(a) provision of a support having a surface area which contains a plurality of individual reaction areas,
(b) location-resolved synthesis of nucleic acid fragments having in each case different base sequences in several of the individual reaction areas, and
(c) detachment of the nucleic acid fragments from individual reaction areas.

The base sequences of the nucleic acid fragments synthesized in individual reaction areas are preferably chosen such that they can assemble to form a nucleic acid double strand hybrid. The nucleic acid fragments can then be detached in step (c) in one or more steps under conditions such that a plurality, i.e. at least some of the detached nucleic acid fragments assemble to form a nucleic acid double strand hybrid. Subsequently, the nucleic acid fragments forming one strand of the nucleic acid double strand hybrid can at least partially be linked covalently to one another. This may be carried out by enzymatic treatment, for example using ligase, or/and filling in gaps in the strands using DNA polymerase.

The method comprises within the framework of a modular system the synthesis of very many individual nucleic acid strands which serve as building blocks and, as a result, a double-stranded nucleic acid sequence which can be more than 100,000 base pairs in length is generated, for example in a microfluidic reaction support.

The highly complex synthetic nucleic acid which preferably consists of DNA is produced according to the method and according to the following principle: first, relatively short DNA strands are synthesized in a multiplicity of reaction areas on a reaction support by in situ synthesis. This may take place, for example, using the supports described in the patent applications DE 199 24 327.1, DE 199 40 749.5, PCT/EP99/06316 and PCT/EP99/06317. In this connection, each reaction area is suitable for the individual and specific synthesis of an individual given DNA sequence of approx. 10-100 nucleotides in length. These DNA strands form the building blocks for the specific synthesis of very long DNA molecules. The fluidic microprocessor used here may carry reaction spaces specially designed for the application.

The DNA synthesis itself is thus carried out by following the automated solid phase synthesis but with some novel aspects: the "solid phase" in this case is an individual reaction area on the surface of the support, for example the wall of the reaction space, i.e. it is not particles introduced into the reaction space as is the case in a conventional synthesizer. Integration of the synthesis in a microfluidic reaction support (e.g. a structure with optionally branched channels and reaction spaces) makes it possible to introduce the reagents and other components such as enzymes.

After synthesis, the synthesized building blocks are detached from said reaction areas. This detachment process may be carried out location- or/and time-specifically for individual, several or all DNA strands.

In a preferred variant of the method it is provided for a plurality of reaction areas to be established and utilized within a fluidic space or compartment so that the DNA strands synthesized therein can be detached in one operation step and taken away from the compartment which fluidically connects the reaction areas.

Subsequently, suitable combinations of the detached DNA strands are formed. Single-stranded or/and double-stranded building blocks are then assembled, for example, within a reaction space which may comprise one or more reaction areas for the synthesis. Expediently, the sequence of the individual building blocks is chosen such that, when bringing the individual building blocks into contact with one another, regions complementary to one another are available at the two ends brought together, in order to make possible specific attachment of further DNA strands by hybridizing said regions. As a result, longer DNA hybrids are formed. The phosphorus diester backbone of these DNA hybrids may be covalently closed, for example by ligases, and possible gaps in the double strand may be filled in in a known manner enzymatically by means of polymerases. Single-stranded regions which may be present may be filled in by enzymes (e.g. Klenow fragment) with the addition of suitable nucleotides. Thus longer DNA molecules are formed. By bringing together clusters of DNA strands synthesized in this way within reaction spaces it is in turn possible to generate longer part sequences of the final DNA molecule. This may be done in stages, and the part sequences are put together to give ever longer DNA molecules. In this way it is possible to generate very long DNA sequences as completely synthetic molecules of more than 100,000 base pairs in length.

The amount of individual building blocks which is required for a long synthetic DNA molecule is dealt with in the reaction support by parallel synthesis of the building blocks in a location- or/and time-resolved synthesis process. In the preferred embodiment, this parallel synthesis is carried out by light-dependent location- or/and time-resolved DNA synthesis in a fluidic microprocessor which is also described in the patent applications DE 199 24 327.1, DE 199 40 749.5, PCT/EP99/06316 and PCT/EP99/06317.

The miniaturized reaction support here causes a reduction in the amount of starting substances by at least a factor of 1000 compared with a conventional DNA synthesizer. At the same time, an extremely high number of nucleic acid double strands of defined sequence is produced. Only in this way is it possible to generate a very large variety of individual building blocks, which is required for the synthesis of long DNA molecules, by using an economically sensible amount of resources. The synthesis of a sequence of 100,000 base pairs, composed of overlapping building blocks of 20 nucleotides in length, requires 10,000 individual building blocks. This can be achieved using appropriately miniaturized equipment in a highly parallel synthesis process.

For efficient processing of genetic molecules and systematic inclusion of all possible variants it is necessary to produce the individual building block sequences in a flexible and economic way. This is achieved by the method preferably by using a programmable light source matrix for the light-dependent location- or/and time-resolved in situ synthesis of the DNA strands, which in turn can be used as building blocks for the synthesis of longer DNA strands. This flexible synthesis allows free programming of the individual building block sequences and thus also generation of any variants of the part sequences or the final sequence, without the need for substantial modifications of system components (hardware). This programmed synthesis of the building blocks and thus the final synthesis products makes it possible to systematically process the variety of genetic elements. At the same time, the use of computer-controlled programmable synthesis allows automation of the entire process including communication with appropriate databases.

With a given target sequence, the sequence of the individual building blocks can be selected efficiently, taking into account biochemical and functional parameters. After putting in the target sequence (e.g. from a database), an algorithm makes out suitable overlapping regions. Depending on the task, different amounts of target sequences can be produced, either within one reaction support or spread over a plurality of reaction supports. The hybridization conditions for formation of the hybrids, such as, for example, temperature, salt concentrations, etc., are adjusted to the available overlap regions by an appropriate algorithm. Thus, maximum attachment specificity is ensured. In a fully automatic version, it is also possible to take target sequence data directly from public or private databases and convert them into appropriate target sequences. The products generated may in turn be introduced optionally into appropriately automated processes, for example into cloning in suitable target cells.

Synthesis in stages by synthesizing the individual DNA strands in reaction areas within enclosed reaction spaces also allows the synthesis of difficult sequences, for example those with internal repeats of sequence sections, which occur, for example, in retroviruses and corresponding retroviral vectors. The controlled detachment of building blocks within the fluidic reaction spaces makes a synthesis of any sequence possible, without problems being generated by assigning the overlapping regions on the individual building blocks.

The high quality requirements necessary for synthesizing very long DNA molecules can be met inter alia by using real-time quality control. This comprises monitoring the location-resolved building block synthesis, likewise detachment and assembly up to production of the final sequence. Then all processes take place in a transparent reaction support. In addition, the possibility to follow reactions and fluidic processes in transmitted light mode, for example by CCD detection, is created.

The miniaturized reaction support is preferably designed such that a detachment process is possible in the individual reaction spaces and thus the DNA strands synthesized on the reaction areas located within these reaction spaces are detached individually or in clusters. In a suitable embodiment of the reaction support it is possible to assemble the building blocks in reaction spaces in a process in stages and also to remove building blocks, part sequences or the final product or else to sort or fractionate the molecules.

The target sequence, after its completion, may be introduced as integrated genetic element into cells by transfer and thereby be cloned and studied in functional studies. Another possibility is to firstly further purify or analyze the synthesis product, a possible example of said analysis being sequencing. The sequencing process may also be initiated by direct coupling using an appropriate apparatus, for example using a device described in the patent applications DE 199 24 327.1, DE 199 40 749.5, PCT/EP99/06316 and PCT/EP99/06317 for the integrated synthesis and analysis of polymers. It is likewise conceivable to isolate and analyze the generated target sequences after cloning.

The method of the invention provides via the integrated genetic elements generated therewith a tool which, for the further development of molecular biology, includes biological variety in a systematic process. The generation of DNA molecules with desired genetic information is thus no longer the bottleneck of molecular biological work, since all molecules, from small plasmids via complex vectors to mini chromosomes, can be generated synthetically and are available for further work.

The production method allows generation of numerous different nucleic acids and thus a systematic approach for questions concerning regulatory elements, DNA binding sites for regulators, signal cascades, receptors, effect and interactions of growth factors, etc.

The integration of genetic elements into a fully synthetic complete nucleic acid makes it possible to further utilize known genetic tools such as plasmids and vectors and thus to build on the relevant experience. On the other hand, this experience will change rapidly as a result of the intended optimization of available vectors, etc. The mechanisms which, for example, make a plasmid suitable for propagation in a particular cell type can be studied efficiently for the first time on the basis of the method of the invention.

This efficient study of large numbers of variants makes it possible to detect the entire combination space of genetic elements. Thus, in addition to the at the moment rapidly developing highly parallel analysis (inter alia on DNA arrays or DNA chips), the programmed synthesis of integrated genetic elements is created as a second important element. Only both elements together can form the foundation of an efficient molecular biology.

The programmed synthesis of appropriate DNA molecules makes possible not only random composition of the coding sequences and functional elements but also adaptation of the intermediate regions. This may rapidly lead to minimal vectors and minimal genomes, whose small size in turn generates advantages. As a result, transfer vehicles such as, for example, viral vectors can be made more efficient, for example when using retroviral or adenoviral vectors.

In addition to the combination of known genetic sequences, it is possible to develop novel genetic elements which can build on the function of available elements. Especially for such developmental work, the flexibility of the system is of enormous value.

The synthetic DNA molecules are in each stage of the development of the method described here fully compatible with the available recombination technology. For "traditional" molecular biological applications it is also possible to provide integrated genetic elements, for example by appropriate vectors. Incorporation of appropriate cleavage sites even of enzymes little used so far is not a limiting factor for integrated genetic elements.

Improvements in Comparison with Prior Art

This method makes it possible to integrate all desired functional elements as "genetic modules" such as, for example, genes, parts of genes, regulatory elements, viral packaging signals, etc. into the synthesized nucleic acid molecule as carrier of genetic information. This integration leads to inter alia the following advantages:

It is possible to develop therewith extremely functionally integrated DNA molecules, unnecessary DNA regions being removed (minimal genes, minimal genomes).

The free combination of the genetic elements and also modifications of the sequence such as, for example, for adaptation to the expressing organism or cell type (codon usage) are made possible as well as modifications of the sequence for optimizing functional genetic parameters such as, for example, gene regulation.

Modifications of the sequence for optimizing functional parameters of the transcript, for example splicing, regulation at the mRNA level, regulation at the translation level, and, moreover, the optimization of functional parameters of the gene product, such as, for example, the amino acid sequence (e.g. antibodies, growth factors, receptors, channels, pores, transporters, etc.) are likewise made possible.

On the whole, the system created by the method is extremely flexible and allows in a manner previously not available the programmed production of genetic material under greatly reduced amounts of time, materials and work needed.

Using the available methods, it has been almost impossible to specifically manipulate relatively large DNA molecules of several hundred kbp, such as chromosomes for example. Even more complex (i.e. larger) viral genomes of more than 30 kbp (e.g. adenoviruses) are difficult to handle and to manipulate using the classical methods of gene technology.

The method of the invention leads to a considerable shortening up to the last stage of cloning a gene: the gene or the genes are synthesized as DNA molecule and then (after suitable preparation such as purification, etc.) introduced directly into target cells and the result is studied. The multi-stage cloning process which is mostly carried out in microorganisms such as E. coli (e.g. DNA isolation, purification, analysis, recombination, cloning in bacteria, isolation, analysis, etc.) is thus reduced to the last transfer of the DNA molecule into the final effector cells. For synthetically produced genes or gene fragments clonal propagation in an intermediate host (usually E. coli) is no longer required. This avoids the danger of the gene product destined for the target cell exerting a toxic action on the intermediate host. This is distinctly different from the toxicity of some gene products, which, when using classical plasmid vectors, frequently leads to considerable problems for cloning of the appropriate nucleic acid fragments.

Another considerable improvement is the reduction in time and the reduction in operational steps to after the sequencing of genetic material, with potential genes found being verified as such and cloned. Normally, after finding interesting patterns, which are possible open reading frames (ORF), probes are used (e.g. by means of PCR) to search in cDNA libraries for appropriate clones which, however, need not contain the whole sequence of the mRNA originally used in their production. In other methods, an expression gene library is searched by means of an antibody (screening). Both methods can be shortened very substantially using the method of the invention: if a gene sequence determined "in silico" is present (i.e. after detection of an appropriate pattern in a DNA sequence by the computer) or after decoding a protein sequence, an appropriate vector with the sequence or variants thereof can be generated directly via programmed synthesis of an integrated genetic element and introduced into suitable target cells.

The synthesis taking place in this way of DNA molecules of up to several 100 kbp allows the direct complete synthesis of viral genomes, for example adenoviruses. These are an important tool in basic research (inter alia gene therapy) but, due to the size of their genome (approx. 40 kbp), are difficult to handle using classical genetic engineering methods. As a result, the rapid and economic generation of variants for optimization in particular is greatly limited. This limitation is removed by the method of the invention.

The method leads to integration of the synthesis, detachment of synthesis products and assembly to a DNA molecule being carried out in one system. Using production methods of microsystem technology, it is possible to integrate all necessary functions and process steps up to the purification of the final product in a miniaturized reaction support. These may be synthesis areas, detachment areas (clusters), reaction spaces, feeding channels, valves, pumps, concentrators, fractionation areas, etc.

Plasmids and expression vectors may be prepared directly for sequenced proteins or corresponding part sequences and the products may be analyzed biochemically and functionally, for example by using suitable regulatory elements. This omits the search for clones in a gene library. Correspondingly, ORFs from sequencing work (e.g. Human Genome Project) can be programmed directly into appropriate vectors and be combined with desired genetic elements. An identification of clones, for example by complicated screening of cDNA libraries, is removed. Thus, the flow of information from sequence analysis to function analysis has been greatly reduced, because on the same day on which an ORF is present in the computer due to analysis of primary data, an appropriate vector including the putative gene can be synthesized and made available.

Compared with conventional solid-phase synthesis for obtaining synthetic DNA, the method according to the invention is distinguished by a small amount of material needed. In order to produce thousands of different building blocks for generating a complex integrated genetic element of several 100,000 kbp in length, in an appropriately parallelized format and with appropriate miniaturization (see exemplary embodiments), a microfluidic system needs markedly fewer starting substances for an individual DNA oligomer than a conventional solid-phase synthesis apparatus (when using a single column). Here, microliters compare with the consumption of milliliters, i.e. a factor of 1000.

Taking into account the newest findings in immunology, the presented method allows an extremely efficient and rapid vaccine design (DNA vaccines).

EXEMPLARY EMBODIMENTS

To carry out the method, the present invention requires the provision of a large number of nucleic acid molecules, usually DNA, whose sequence can be freely determined. These building blocks must have virtually 100% identical sequences within one building block species (analogously to the synthesis performance of conventional synthesizers). Only highly parallel synthesis methods are suitable for generating the required variance. In order for the system to be able to work flexibly and, despite the necessary multiplicity of different building blocks to be synthesized, to require as little space and as few reagents as possible, the method is preferably carried out in a microfluidic system within which the individual sequences are produced in a determinable form. Two types of programmed synthesis are suitable for systems of this kind, which are also described in the patent applications DE 199 24 327.1, DE 199 40 749.5, PCT/EP99/06316 and PCT/EP99/06317: these are first the synthesis by programmable fluidic individualization of the reaction areas and, secondly, the synthesis by programmable light-dependent individualization of the reaction areas.

In both variants, synthesis is carried out in a microfluidic reaction support. The design of this reaction support may provide in the system for the bringing together in stages the detached synthesis products, i.e. building blocks, by collecting the nucleic acid strands, after detaching them, in appropriate reaction areas and the assembly taking place there. Groups of such assembly areas may then for their part be brought into contact again with one another so that during the course of a more or less long cascade the final synthesis products are produced: genetic information carriers in the form of DNA molecules. The following variants are suitable here:

Either synthesis, detachment and assembly are carried out chronologically but spatially integrated in a microfluidic reaction support or synthesis, detachment and assembly are carried out partially in parallel in one or more microfluidic reaction supports. It is furthermore possible that the microfluidic reaction support contains only reaction areas for the programmed synthesis and that subsequently detachment and elution into a reaction vessel for the assembly are carried out.

In the case of very large DNA molecules, synthesis, detachment and assembly can be supplemented by condensation strategies which prevent break-up of the molecules. This includes, for example, the use of histones (nuclear proteins which make condensation of the chromosomes in the nucleus possible in eukaryotes), the use of topoisomerases (enzymes for twisting DNA in eukaryotes and prokaryotes) or the addition of other DNA-binding, stabilizing and condensing agents or proteins. Depending on the design of the reaction support, this may take place by integrating the condensation reaction in another reaction chamber provided therefor or by addition during the combination and assembly in stages of the building blocks.

The free choice of sequence is of essential importance for the controlled and efficient building block assembly in stages to the final product. For the choice of overlapping complementary ends influences the specificity of the assembly and the overall biochemical conditions (salt concentration, temperature, etc.). When providing a sequence for the gene of interest and after automatic or manual selection of the other genetic elements (regulatory regions, resistance genes for cloning, propagation signals, etc.) for determination of the final product (e.g. a plasmid vector), the provided sequence is fragmented into suitable building blocks which are then synthesized in the required number of reaction supports. The fragments or their overlap regions to be hybridized are chosen such that the conditions for hybridizing are as similar as possible (inter alia GC: AT ratio, melting points, etc.).

Further extension of the system provides for elements for purification and isolation of the product forming, which are likewise designed by microfluidics or microsystem technology. Said elements may be, for example, methods in which the final double-stranded DNA after its synthesis using fluorescent synthons must have a particular total fluorescence. When using proteins with condensing action, these proteins, where appropriate, may also carry a fluorescent label which is preferably detectable separately (reference signal). It is then possible to sort the mixture of final reaction product in the reaction support structures according to fluorescence (see Chou et al., Proceedings of the National Academy of Science PNAS 96:11-13, 1999). Thus a sufficient quality is achieved in order to directly provide a product for further work.

Information from sequencing projects, which is present in databases, may be studied for genes fully automatically (computer-assisted). Identified or putative genes (ORFs) are converted into completely synthetic DNA which may contain, where appropriate, regulatory and other genetic elements which seem suitable, so that, for example, one or more vectors are generated. The product is either made available (e.g. as pure DNA) or directly introduced to functional studies, inter alia by transfer into suitable target cells. The information may come from public databases, from work of decentralized users or from other sources, for example the method described in the patent applications DE 199 24 327.1 and DE 199 40 749.5.

It may be of interest that a variance of randomized sequence occurs at a particular site or sites of the target sequence. An example is the testing of variants of a binding site into which, for example over an area of 20 amino acids, i.e. 60 nucleotides, random variations of nucleotides were incorporated. This may take place in an embodiment in that during the synthesis process, after activating a reaction area, a mixture of synthons is added so that all added synthons can hybridize in a statistically distributed manner. A modification of this process may provide for DNA building blocks of different length to be used at a particular position of the target sequence, for example by producing different building blocks on different reaction areas, which show the same sequence for overlapping and hybridization.

What is claimed is:

1. A method for optimizing the functional genetic parameters of genetic elements, comprising:
   (a) providing a digital sequence of a variant of a known genetic element,
   (b) fragmenting the digital sequence of step (a) into a plurality of suitable complementary oligomeric building blocks that can assemble to form a nucleic acid double-stranded hybrid,
   (c) synthesizing the plurality of oligomeric building blocks by parallel synthesis steps, wherein each oligomeric building block is synthesized on a different area of a common support,
   (d) detaching the oligomeric building blocks from the support,
   (e) bringing the oligomeric building blocks into contact with one another,
   (f) linking the oligomeric building blocks enzymatically to form the variant of the known genetic element,
   (g) introducing the variant directly into a target cell and observing a result, and
   (h) comparing the result obtained in step (g) with a reference result of the known genetic element.

2. The method according to claim 1, wherein the genetic elements are selected from the group consisting of genes, parts of genes, regulatory elements or viral packaging signals.

3. The method according to claim 1, wherein the digital sequences are derived from a database.

4. Method according to claim 1, wherein the variants are generated by random composition.

5. The method according to claim 1, wherein the variants are generated for optimizing codon usage.

6. The method according to claim 1, wherein in step (b) biochemical and functional parameters are taken into account for generating the variants.

\* \* \* \* \*